United States Patent
Brown

(10) Patent No.: US 7,275,637 B2
(45) Date of Patent: Oct. 2, 2007

(54) MULTI-CHANNEL CONVEYOR BELT CONDITION MONITORING

(76) Inventor: Barry Charles Brown, 42/3482 Main Beach Parade, Main Beach QLD 4217 (AU)

( * ) Notice: Subject to any disclaimer, the term of this patent is extended or adjusted under 35 U.S.C. 154(b) by 0 days.

(21) Appl. No.: 11/361,040

(22) Filed: Feb. 24, 2006

(65) Prior Publication Data
US 2006/0202684 A1    Sep. 14, 2006

(30) Foreign Application Priority Data
Feb. 24, 2005    (AU) ............................... 2005900851

(51) Int. Cl.
*B65G 43/00*    (2006.01)
(52) U.S. Cl. ................ 198/810.02; 198/502.1
(58) Field of Classification Search ........ 198/810.02, 198/502.1; 340/676; 324/226, 232
See application file for complete search history.

(56) References Cited

U.S. PATENT DOCUMENTS 3,834,524 A * 9/1974 Ratz et al. ............. 198/810.02
3,899,071 A * 8/1975 Duffy ..................... 198/810.02
4,437,563 A * 3/1984 Oriol ...................... 198/810.02
4,621,727 A * 11/1986 Strader ................... 198/810.02
4,854,446 A * 8/1989 Strader ................... 198/810.02
6,291,991 B1 * 9/2001 Schnell .................. 198/810.02

* cited by examiner

*Primary Examiner*—James R. Bidwell
(74) *Attorney, Agent, or Firm*—Arent Fox LLP

(57) ABSTRACT

A method of monitoring the condition of magnetically permeable reinforcing cords of a conveyor belt is disclosed. The cords are longitudinally magnetized with a substantially unidirectional magnetic field. The conveyor belt is then moved relative to a plurality of magnetic sensors spaced apart and extending transversely relative to the conveyor belt. Then the sensors are interrogated at spaced apart intervals of time and used to detect the presence of a north polarity fringing magnetic field, a south polarity fringing magnetic field, or no fringing magnetic field, the output of each of the senses being recorded. Alternatively, a wave form of the voltage or current induced in the sensors can be derived therefrom and the waveform used to represent a north polarity fringing magnetic field, a south polarity fringing magnetic filed, or no fringing magnetic field, the waveform being recorded. A method of generating a computer display to represent the condition of the magnetically permeable reinforcing chords is also disclosed.

13 Claims, 4 Drawing Sheets

Figure 4:
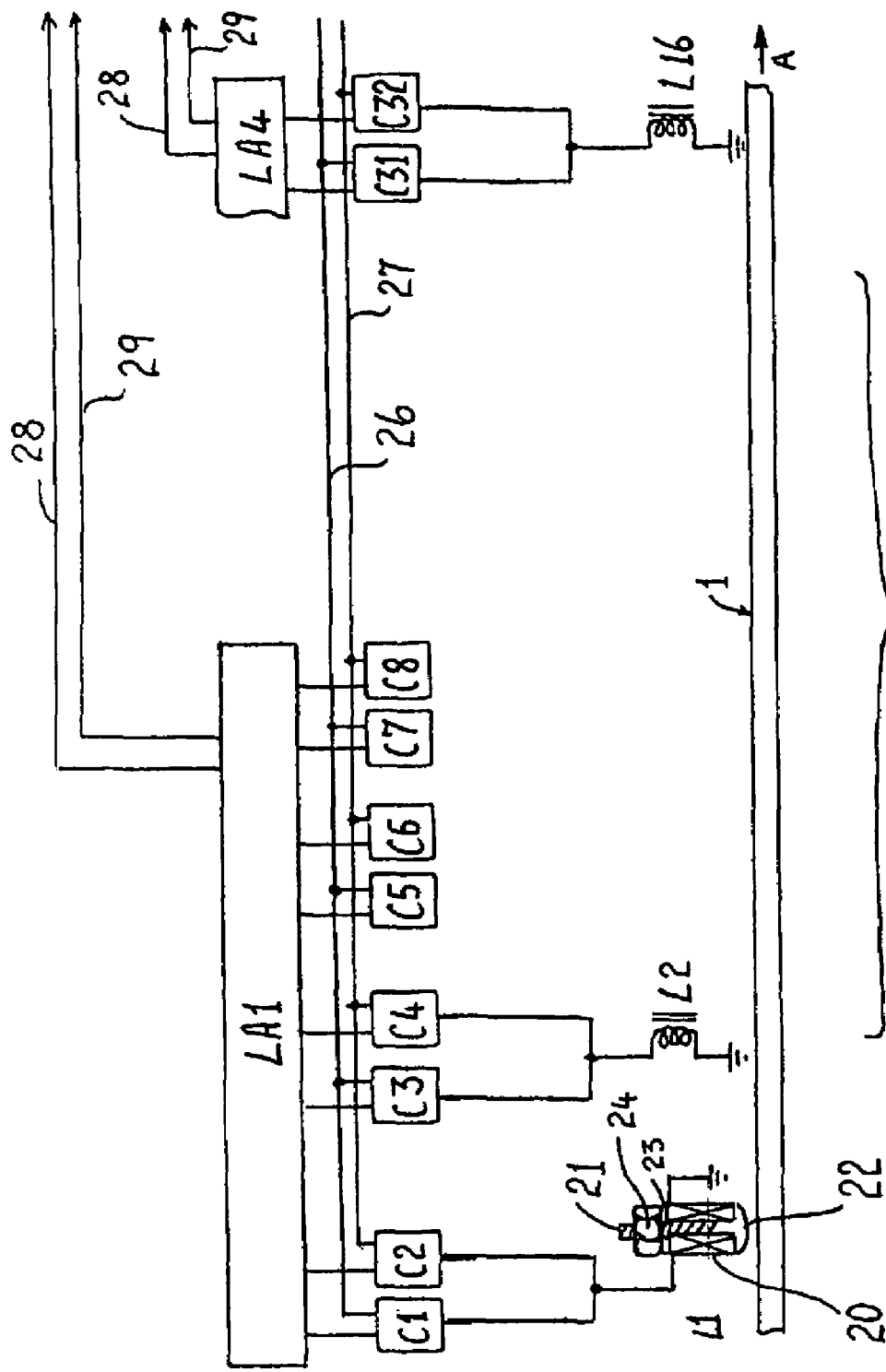

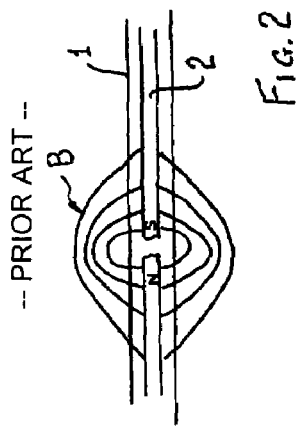
Fig. 2 -- PRIOR ART --
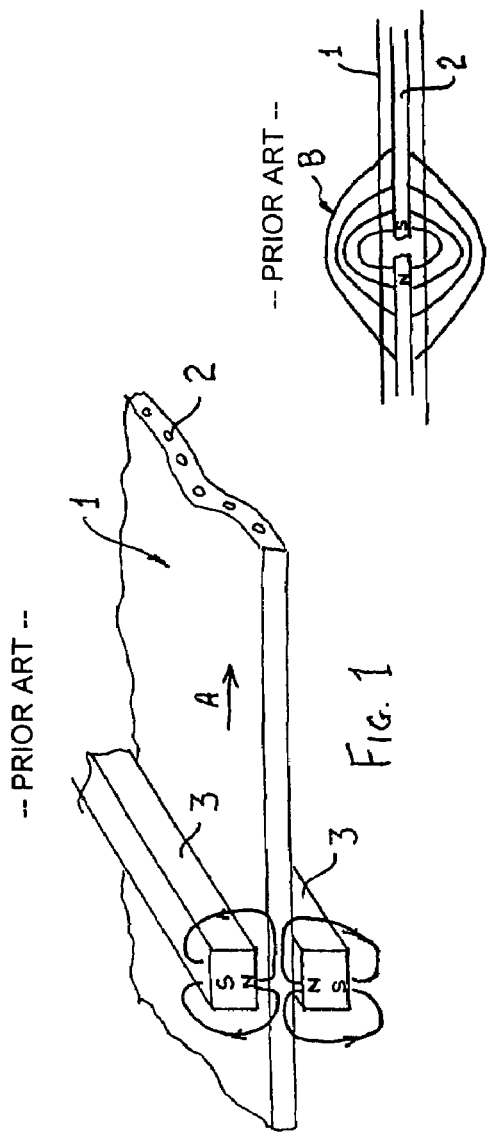
Fig. 1 -- PRIOR ART --
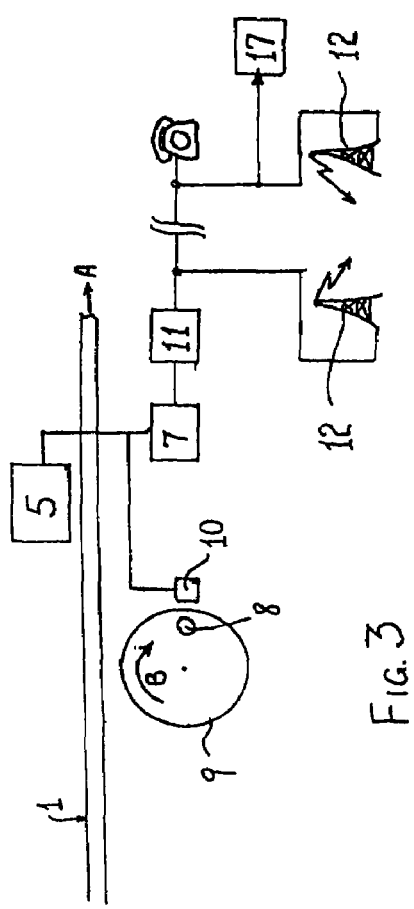
Fig. 3

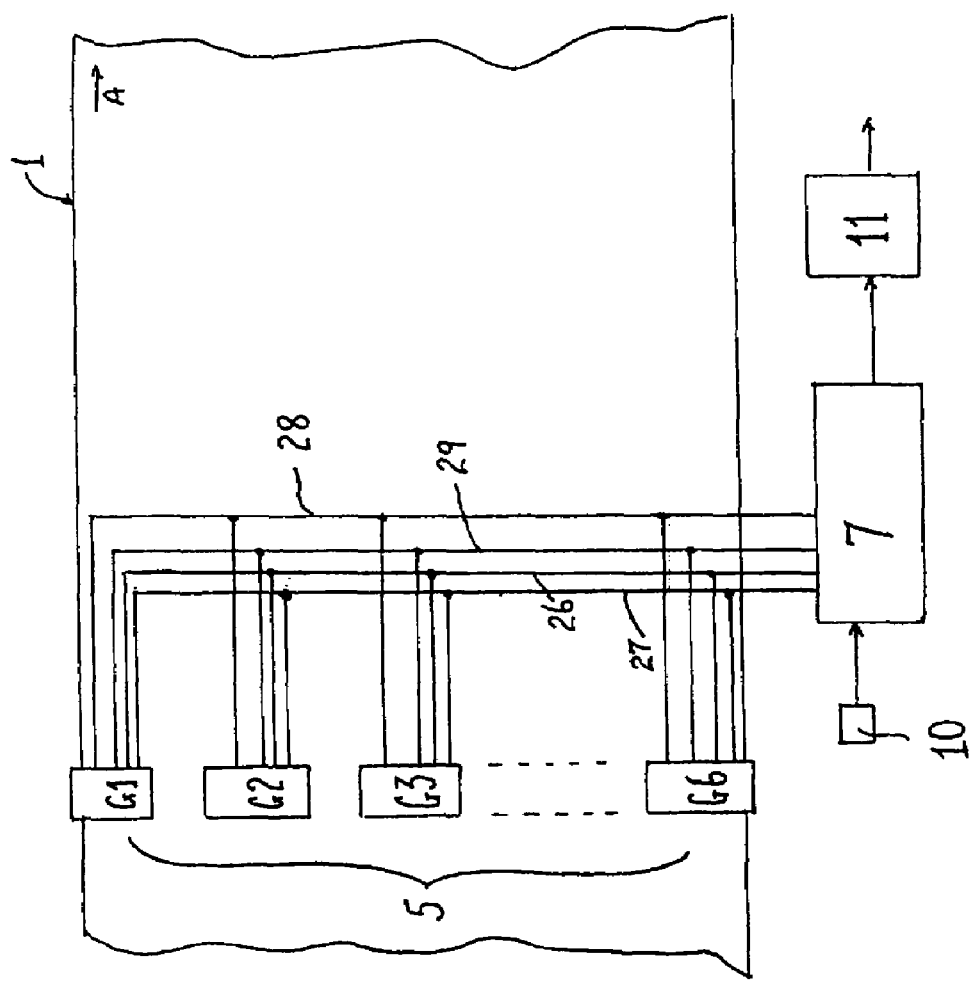

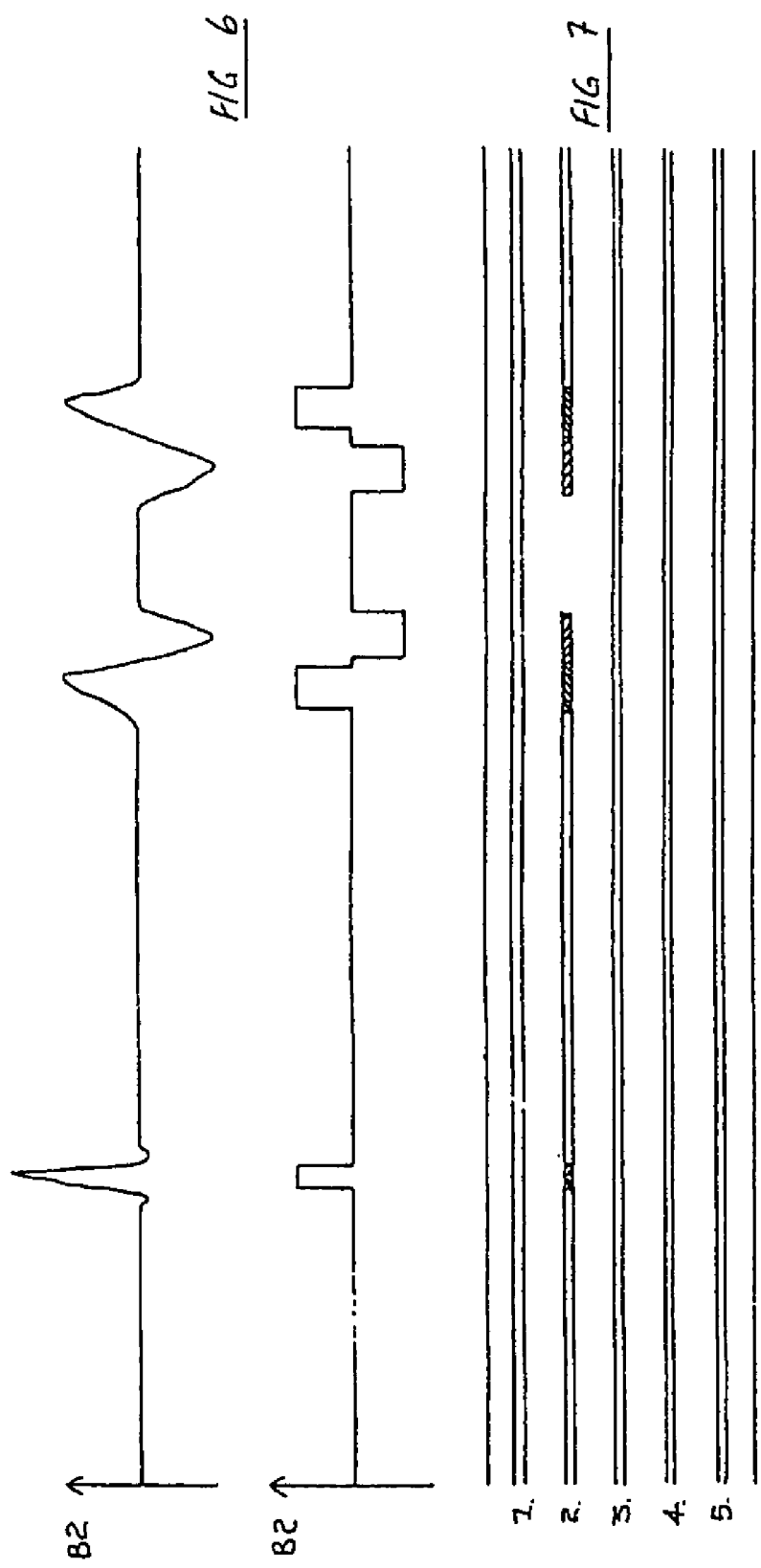

MULTI-CHANNEL CONVEYOR BELT CONDITION MONITORING

The present invention relates to the monitoring of belt conveyors having magnetically permeable reinforcing cords.

The traditional conveyor belt consists of a fabric tension member covered with top and bottom elastomeric covers. It is known that this type of belting stretches and is unsuitable for applications involving long conveyor flight lengths, significant lift and high tonnage product throughput. Is this case, the stretch in the belting renders it incapable of being driven by the drive pulley(s), through lack of grip.

To overcome this problem, a type of belting was devised which uses a multitude of high tensile longitudinal steel ropes or cords as the tension member. The cords have low elongation and facilitate much higher tension applications. The steel cords can be damaged or broken through product impact at the load point, and by other mechanisms. Where a significant number of the cords are damaged in a region which extends transversely in the belting, the tension capability of the belt carcass is compromised, and this can lead to catastrophic failure. Cord damage can be repaired and in cases where a large amount of damage has occurred, the whole area of damage can be cut out of the belting and replaced with a join or splice in the belt. This fact allows for preventive maintenance techniques to be applied, which enables the belt operator to maintain over time, the integrity of the belting.

Since steel cord belting is capable of operating under very high tensions, of the order of 8,000 kN per meter of belt width and beyond, and can have total belt thickness approaching 50 mm or more, the mass or volume per unit length of the belting can be significant. While the belt manufacturing process is largely continuous, the belting must be cut up into 'rolls' of manageable size or mass, as dictated by intended modes of transport. Accordingly, a typical roll of steel cord belting might contain 100-300 m of belt.

Obviously, where the 'tail' (load point) and 'head' (discharge point) of a conveyor are many kilometers apart, a multiple number of rolls of belting will be required to make up the 'endless belt length'. This is achieved by joining rolls using vulcanised joints or splices. A long conveyor may contain fifty or more splices in the endless belt length. The strength of the splices can be affected by the same destructive forces as act on the parent belt, and there is the additional problem of loss of adhesion in the splice zone.

Preventive maintenance requires that the condition of the cords and splices in the belt be known, and thus the number of damaged cords at any one location needs to be assessed, along with cord damage and movement within a splice. Because this kind of damage is not always visible at the belt surface, and for a variety of other reasons, including belt speed, poor lighting and time restrictions, reliable visual assessment of belt condition is not possible. This fact has given rise to the development of a variety of non-invasive condition monitoring techniques used to assess carcass and splice condition, with the belt running fully loaded, at full production speed.

As seen in FIGS. 1 and 2, a prior art method employed involves the uniform longitudinal magnetization of the cords 2, while the conveyor belt 1 is running. This is done using a steady-state magnetic field provided by permanent or electro magnets 3. Where cords are damaged, there exists a fringing magnetic field, which can be detected with a suitable magnetic sensor 5, fitted across the belt, which is excited by these fringing fields as the belt passes the scanning location. The number and location of cord ends in the splices can be determined using the same effect. The voltage output from the sensors is commonly delivered to a paper chart recorder or digitised and stored in data file form called 'break traces', using an industrial computer 7.

A tachometer pulse is derived by affixing a small permanent magnet 8 to a roller or drum, typically a wing idler roller 9, which is driven by the target belt. As this roller rotates, the magnet induces a voltage spike in a suitable sensor 10, preferably an inductor, mounted in close proximity to the roller 9, at the rate of one spike per revolution. The circumference of the roller is noted. The resultant voltage spikes are shaped using suitable circuitry and thus a pulse train is produced, the frequency of which is proportional to belt speed. Using the known circumference of the roller 9, a simple calculation provides longitudinal distance information along the belt.

Waveform viewing software is then needed to view these 'break traces'. Waveform viewing software for displaying traces is known.

Because the belt 1 is left magnetised, the fringing magnetic fields are also absolute location markers, which can be used by belt maintenance personnel to find events exactly, using a magnetometer, where there may be confusion about the precise location of an event.

The Conveyor Belt Monitoring (CBM) non-destructive condition monitoring system employs this technique and has been well described in the literature.

In the CBM system, the sensing head divides the belting into three longitudinal strips spaced across the belt width, giving Left, Centre and Right 'break traces'. Lateral resolution of a third of the belt width is inadequate to quantify cord damage sufficiently well, so physical inspection of at least some of the damage is required to 'calibrate' the break traces.

An alternative prior art technique, the Belt C.A.T. scanner, uses multiple sensors across the belt width, which provides for much greater resolution, and aids in quantification of cord and splice damage.

A shortcoming of both systems is the fact that a skilled technician is required on-site, together with complex and often fragile equipment, to perform the measurements. This is particularly difficult where the conveyors are sited in very remote locations and in less than hospitable environments. Significant cost is also involved in getting the technician and equipment to site and providing accommodation and transport.

To overcome this problem, the prior art CBM Remote system was developed, which requires that the magnetizing, sensing and tachometer equipment is permanently fitted to the conveyor and accessed using a dedicated industrial computer and on-site Local Area Network, standard telephone line or the cellular phone networks for example, by using a suitable modem 11 and the public telephone network including mobile phone towers 12, as illustrated in FIG. 3. The data is telephonically transferred, either discretely or via the Internet and loaded into a second computer 17. In this way, a scan can be performed at any time from anywhere, usually a laboratory located in a major city somewhere in the world. For this system to operate effectively, the data file size must be sufficiently small to allow for transfer of the file back for analysis, in a reasonable time. A typical CBM Remote file size for a very long belt, say 22,000 m, is approximately 6 Mb which takes about twenty minutes to download on a typical average quality phone line.

Because the Belt C.A.T. scanner uses a multitude of sensing devices, and a very high sample rate, the resulting file size (of the order of Gb) is too large to transmit in a reasonable time. Thus, this scanning system is not able to be used for remote scanning.

In both the Belt C.A.T. and CBM systems, the voltage output from each sensor is digitised and stored using an A/D converter with typically 12 bit resolution at a minimum sample rate of 400 s/s (samples per second) extending up to 750 ks/s (thousand samples per second). For a long belt the Belt C.A.T. scanner will produce a data file size of typically greater than 2 Gb (Gigabytes). This file requires a significant amount of processing before it is in a form which can be analysed by the technician, to allow an assessment of belt carcass and splice condition to be made. This is commonly needed to be done overnight, or at some later date, which means that an instant result is not obtained. Also, the discovery of a data acquisition problem, post processing, in a Belt C.A.T file is highly inconvenient, necessitating a return visit to site.

The genesis of the present invention is a desire to reduce the volume of data which needs to be transmitted from a remote site in order to permit the condition of the conveyor belt at that site to be assessed.

In accordance with a first aspect of the present invention there is disclosed a method of monitoring the condition of magnetically permeable reinforcing cords of a conveyor belt, said method comprising the steps of:

(i) longitudinally magnetizing said cords with a substantially constant unidirectional magnetic field, (ii) moving said conveyor belt relative to a plurality of magnetic sensors spaced apart and extending transversely relative to said belt, (iii) interrogating said sensors at spaced apart intervals of time, (iv) using said sensors to each detect the presence of a north polarity fringing magnetic field, a south polarity fringing magnetic field, or no fringing magnetic field, and (v) recording the output of each said sensor.

In accordance with a second aspect of the present invention there is disclosed a method of monitoring the condition of magnetically permeable reinforcing cords of a conveyor belt, said method comprising the steps of:

(i) longitudinally magnetising said cords with a substantially constant unidirectional magnetic field, (ii) moving said conveyor belt relative to a plurality of magnetic sensors spaced apart and extending transversely relative to said belt, (iii) deriving from said sensors a waveform of the voltage or current induced therein, (iv) using said waveform to represent a north polarity fringing magnetic field, a south polarity fringing magnetic field or no fringing magnetic field, and (v) recording said waveform.

In accordance with a third aspect of the present invention there is disclosed a method of generating a computer display to represent the condition of magnetically permeable reinforcing cords of a conveyor belt, said method comprising the steps of:

(i) generating a plurality of longitudinally extending strips each corresponding to one of said cords, (ii) detecting on said conveyor belt for substantially each said cord the absence of a fringing magnetic field, the presence of a north polarity fringing magnetic field, or the presence of a south polarity fringing magnetic field, (iii) for each said strip providing a first indicium to the location thereon corresponding to each detected north polarity fringing magnetic field, (iv) for each said strip providing a second indicium at the location thereon corresponding to each detected south polarity fringing magnetic field, and (v) generating a computer display to show said strips and indicia.

A computer display and apparatus are also disclosed.

Some embodiments of the present invention will now be described with reference to the drawings in which:

FIG. 1 is a perspective view of a conveyor belt showing the prior art uniform magnetisation technique, FIG. 2 shows the conventional fringing magnetic field B at a break in a magnetised steel cord conveyor belt cord, FIG. 3 is a schematic block diagram of the remote data gathering arrangement used in the present invention, FIG. 4 is a schematic block diagram of a new sensor arrangement of the preferred embodiment, FIG. 5 is a schematic block diagram showing the insertion of the arrangement of FIG. 4 in FIG. 3, FIG. 6 shows two graphs, the upper trace being a conventional output from a sensor monitoring a single damaged cord, the lower trace being a modified data output in accordance with the preferred embodiment, and FIG. 7 is a computer display representing the cord condition corresponding to the lower trace of FIG. 6.

The preferred embodiment of the present invention is based upon the realisation that for an assessment of the condition of a cord (or the location of its end) lying under a sensor, it is not necessary to digitise the conventional analogue voltage waveform. If the number of sensing elements equates to, or is close to, the number of cords in the belt it is simply necessary to determine if there is magnetic activity present in the cord, or not. This reduces the description of the condition of the cord to two states YES or NO, which can be described using one bit of data. In the preferred embodiment of the device three states, YES NORTH POLARITY fringing magnetic field, YES SOUTH POLARITY fringing magnetic field and NO fringing magnetic field are used, which states can be defined with two bits of data. It is essential, for correct understanding of the type of damage present in the cord, or the location of its end, to know the polarity of the fringing magnetic field. It is known from the literature that 'leading' and 'trailing' cord ends produce fringing magnetic fields of opposite polarity.

Turning now to FIG. 4, the modified arrangement for the sensor 5 in accordance with the preferred embodiment is illustrated. For a single group G sixteen inductors L1-L16 are provided. For ease of illustration only the details of the first inductor L1 are shown. Each of the inductors L1-L16 takes the form of a coil 20 wound on a cylindrical bobbin through which is passed a soft iron bolt 21 having a head 22, a washer 23 and a nut 24. The longitudinal axis of the bolt 21 is arranged to be substantially normal to the surface of the conveyor belt 1. One end of the coil 20 is earthed and the other end is connected to a pair of comparators. Thus inductor L1 is connected to comparators C1 and C2, inductor L2 is connected to comparators C3 and C4 and so on with inductor L16 being connected to comparators C31 and C32.

Each comparator C1-C32 is connected to either a variable north polarity threshold input 26 or a variable south polarity threshold input 27. The output of each comparator C1-C32 is connected to corresponding one of four latches LA1-LA4. Thus only comparators C1-C8 are connected to latch LA1 whilst comparators C9-C16 are connected to latch LA2, and so on. The latches LA1-LA4 are provided with corresponding shift register lines 28 and clock lines 29. Each group G has four latches.

Each comparator is latched and transferred into a shift register. The data from all sensors are then clocked out with two bits per sensor.

The inductive sensors L are spaced apart across the belt 1 in equidistant fashion at, say, 25 mm centres. In the presence of a passing fringing magnetic field B as illustrated in FIG. 2, a voltage will be induced in one or more of the sensors L. The polarity of the voltage received from the inductor L is delivered to the corresponding comparator circuit C. Where the voltage delivered by the sensor L exceeds the set threshold of the comparator C, the following latch circuit LA is SET. North polarity and south polarity comparators are provided to deal with the polarity. In the absence of any excitation, both comparators are OFF.

As indicated in FIG. 5, the preferred embodiment has a number of groups G across the belt 1. Each group G contains 16 inductors, 32 comparators and 4 latches, all of which are mounted on a rigid PCB (printed circuit board—not illustrated). As well as these components, the PCB carries a number of busses which are accessed through multi-pin connectors at either end, enabling the groups G to be cascaded to make up the desired active scanning width.

The number of groups G across the belt 1 is varied to match the belt width, plus a margin for belt wander. A typical large sense head would contain 6 groups each group G having 16 inductors L. This provides approximately 2,375 mm of active scanning width.

The cascaded PCB's are mounted on a structural spine and are inserted into a 316 grade stainless steel box section tube of suitable length. The tube is then filled with potting compound, and provided with mounting points to facilitate fixing to the conveyor structure. The composite sense head 5 is accessed via an armoured cable at either end.

The sense head 5 and tacho 10 are connected to the (first) computer 7, which is sited away from the scanning location, typically in a nearby electrical sub-station.

The threshold voltages on threshold inputs 26 and 27 are adjustable by the operator in software, and can be varied to suit the belt being scanned, its speed, the level of magnetisation and the distance of the sensors L from the belt surface. With the correct level of threshold, only the comparators connected to sensors closest to a cord having a fringing magnetic field are turned ON by that passing magnetic field.

The latches LAn for each inductor L are interrogated and reset by the processor using the lines 28 and 29, in order, at a rate of between 100-400 times per second, per inductor. The interrogation rate is operator adjustable in software and is set at the minimum rate required to detect a touching cord break, given the speed of the target belt.

The resultant data creates a single file consisting of, in the case cited above, 96 discrete cord state channels, and an additional channel containing the pulse train derived from the tachometer sensor 10 (FIG. 3), driven by the belt 1, which provides real time longitudinal speed and positional information.

Since the cords 2 are magnetised, as in the CBM system, this magnetisation effectively increases the length of very short events, such as touching breaks, through the effect of 'mutual magnetisation', so sample rates necessary to provide longitudinal resolution down to 1 mm or less in belts travelling at say 8 m/sec, to detect touching breaks, are not needed. In fact, a touching cord break, a short time after magnetisation, can produce a magnetic 'event' in excess of 100 mm in length, (as schematically illustrated in FIG. 2) which requires a sample rate of less than 100 s/s for detection, at that belt speed.

The data is streamed to a suitable data storage device associated with the first computer 7, where it is held until downloaded, as convenient, for analysis.

In order to analyse the data, a proprietary software package is used giving a computer display which is specifically generated for this purpose in accordance with one aspect of the preferred embodiment.

Illustrated in FIG. 6 is a typical result for a damaged cord, in this instance cord No. 2 of FIG. 7. The first trace in FIG. 6 is the induced voltage analogue waveform of the magnetic field B2 in cord No. 2. It is this waveform which is sampled and effectively re-constituted in the prior art procedures.

The second trace in FIG. 6 is the result of the threshold and latching operations carried out by the circuit of FIG. 4. That is, only the presence or absence of a north polarity or south polarity fringing magnetic field is indicated.

The default colour of the lines representing the cords in FIG. 7 is white. Where no magnetic activity is present, the colour of the line for that cord or those cords remains un-changed. Where YES NORTH POLARITY exists, the line colour is changed to say blue (indicated by cross hatching in FIG. 7 which rises to the right), and where YES SOUTH POLARITY exists the colour of the line is changed to say orange (indicated by cross hatching in FIG. 7 which falls to the right).

Thus what the analyst sees in the display of FIG. 7 is an "artist's impression" of the steel cords in the belt, as would be seen if looking down on the belt and looking through the upper belt cover as if it were transparent.

Using this method, the analyst can inform the belt operator where cord damage exists in the belt 1, including the exact number and location of the cords involved, and, where changes are observed over time in the 'signatures' of splices, this too can be reported on very precisely.

In the preferred embodiment, all data gathering and subsequent condition reporting can be done remotely, thereby avoiding the time and expense of repeated visits to the remote sites after the initial installation has been carried out.

Although the present invention was conceived with the intention of being able to reduce the amount of data required to be transmitted from the remote belt site, a consideration of FIGS. 6 and 7 leads to a further development. This is the realisation that the first trace on FIG. 6 effectively constitutes the result of the prior art CBM and Belt C.A.T data acquisition, for example. Therefore if such data, irrespective of how it is gathered or transmitted, is subjected to the threshold and latching techniques disclosed above in relation to FIG. 4, then an output similar to the second trace of FIG. 6 is obtained. As a consequence, this data (however obtained) can be displayed using the display techniques described above in relation to FIG. 7. That is, the techniques described above in relation to the generation of a computer display, are not restricted to data obtained as described above in relation to FIG. 3 but have a wider applicability.

The foregoing describes only one embodiment of the present invention and modifications, obvious to those skilled in the conveyor belt monitoring arts, can be made thereto without departing from the scope of the present invention.

For example, it is desirable that the belt be magnetized in such a way that the fringing magnetic field(s) associated with a single damaged cord is/are sufficiently small to excite only the magnetic sensor positioned adjacent to that damaged cord. This can be done by magnetizing the cords with one polarity, initiating a data capture, and reversing the polarity of the magnetic field. The first full revolution of the belt where the magnetic field is reversed provides data from which correct quantification of the number of damaged cords across the belt at any one location can be accurately determined.

The term "comprising" (and its grammatical variations) as used herein is used in the inclusive sense of "including" or "having" and not in the exclusive sense of "consisting only of".

The invention claimed is:

1. A method of monitoring the condition of magnetically permeable reinforcing cords of a conveyor belt, said method comprising the steps of:
   (i) longitudinally magnetizing said cords with a substantially constant unidirectional magnetic field,
   (ii) moving said conveyor belt relative to a plurality of magnetic sensors spaced apart and extending transversely relative to said conveyor belt,
   (iii) interrogating said sensors at spaced apart intervals of time,
   (iv) using said sensors to each detect the presence of a north polarity fringing magnetic field, a south polarity fringing magnetic field, or no fringing magnetic field, and
   (v) recording the output of each said sensor.

2. The method as claimed in claim 1 including the further step of recording said sensor output as two bits of data.

3. The method as claimed in claim 1 including the further step of transmitting said recorded output to a location remote from said conveyor belt.

4. The method as claimed in claim 3 wherein said transmission is telephonic.

5. The method as claimed in claim 1 including the step of operating said sensors to inductively sense said fringing magnetic field.

6. The method as claimed in claim 5 including the step of providing each said inductive sensor with an elongate permeable core having a longitudinal axis, and positioning each said axis substantially normal to said conveyor belt.

7. A method of monitoring the condition of magnetically permeable reinforcing cords of a conveyor belt, said method comprising the steps of:
   (i) longitudinally magnetising said cords with a substantially constant unidirectional magnetic field,
   (ii) moving said conveyor belt relative to a plurality of magnetic sensors spaced apart and extending transversely relative to said conveyor belt,
   (iii) deriving from said sensors a waveform of the voltage or current induced therein,
   (iv) using said waveform to represent a north polarity fringing magnetic field, a south polarity fringing magnetic field or no fringing magnetic field, and
   (v) recording said waveform.

8. The method as claimed in claim 7 including the further step of recording said waveform as two bits of data.

9. The method as claimed in claim 7 including the further step of transmitting said recorded waveform to a location remote from said conveyor belt.

10. The method as claimed in claim 9 wherein said transmission is telephonic.

11. The method as claimed in claim 7 including the step of operating said sensors to inductively sense said fringing magnetic field.

12. A method of generating a computer display to represent the condition of magnetically permeable reinforcing cords of a conveyor belt, said method comprising the steps of:
   (i) generating a plurality of longitudinally extending strips each corresponding to one of said cords,
   (ii) detecting on said conveyor belt for substantially each said cord the absence of a fringing magnetic field, the presence of a north polarity fringing magnetic field, or the presence of a south polarity fringing magnetic field,
   (iii) for each said strip providing a first indicium at the location thereon corresponding to each detected north polarity fringing magnetic field,
   (iv) for each said strip providing a second indicium at the location thereon corresponding to each detected south polarity fringing magnetic field, and
   (v) generating a computer display to show said strips and indicia.

13. The method as claimed in claim 12, wherein said first indicium is a first colour and said second indicium is a second, contrasting, colour.

* * * * *